United States Patent
Schimitzek

(10) Patent No.: US 6,735,326 B1
(45) Date of Patent: May 11, 2004

(54) METHOD FOR EVALUATING THE HALVES OF SLAUGHTERED ANIMALS BY OPTICAL IMAGE PROCESSING

(75) Inventor: Peter Schimitzek, Geilenkirchen (DE)

(73) Assignee: CSB-System Software-Entwicklung & Unternehmensberatung AG, Geilenkirchen (DE)

(*) Notice: Subject to any disclaimer, the term of this patent is extended or adjusted under 35 U.S.C. 154(b) by 0 days.

(21) Appl. No.: 09/529,775

(22) PCT Filed: Jun. 22, 1999

(86) PCT No.: PCT/DE99/01854

§ 371 (c)(1),
(2), (4) Date: Apr. 12, 2001

(87) PCT Pub. No.: WO00/10396

PCT Pub. Date: Mar. 2, 2000

(30) Foreign Application Priority Data

Aug. 20, 1998 (DE) .......................... 198 37 806

(51) Int. Cl.$^7$ ................................. G06K 9/00
(52) U.S. Cl. ................. 382/110; 382/291; 382/173; 356/918
(58) Field of Search .................. 382/110, 173, 382/291, 100; 348/6.1; 119/14.16; 428/35.6; 452/95; 426/250; 356/918

(56) References Cited

U.S. PATENT DOCUMENTS

| | | | | |
|---|---|---|---|---|
| 5,339,815 A | * | 8/1994 | Liu et al. ................... 600/437 |
| 5,937,080 A | * | 8/1999 | Vogeley et al. ............. 382/110 |
| 5,960,105 A | * | 9/1999 | Brethour ..................... 382/141 |
| 6,023,497 A | * | 2/2000 | Takahashi et al. ........... 378/57 |
| 6,099,473 A | * | 8/2000 | Liu et al. .................... 600/449 |
| 6,198,834 B1 | * | 3/2001 | Belk et al. .................. 382/110 |
| 6,549,289 B1 | * | 4/2003 | Ellis ........................... 356/603 |
| 6,587,575 B1 | * | 7/2003 | Windham et al. ........... 382/110 |
| 2002/0037092 A1 | * | 3/2002 | Craig et al. ................. 382/110 |
| 2003/0072472 A1 | * | 4/2003 | Haagensen et al. ......... 382/110 |

FOREIGN PATENT DOCUMENTS

| | | |
|---|---|---|
| DE | 41 31 556 A | 4/1992 |
| DE | 41 09 345 C2 | 8/1993 |
| DE | 44 08 604 C2 | 5/1996 |
| WO | 98 08088 A | 2/1998 |

* cited by examiner

Primary Examiner—Timothy M. Johnson
Assistant Examiner—Barry Choobin
(74) Attorney, Agent, or Firm—Michael J. Striker

(57) ABSTRACT

The invention relates to a method for evaluating the halves of slaughtered animals by optical image processing. A simple computerized method for sufficiently reliable evaluation is obtained even when the symmetry plane has been missed during cutting of the slaughtered animals due to cutting error by detecting two salient points and a straight line (5) in a photogrammetric reliable manner and by additionally calculating a parallel line (6) and a vertical line (7), wherein the end of the connecting bone (2) on the body side is used as first salient point and the central extension of the back fat (4) is used as a first direction.

5 Claims, 1 Drawing Sheet

METHOD FOR EVALUATING THE HALVES OF SLAUGHTERED ANIMALS BY OPTICAL IMAGE PROCESSING

FIELD OF THE INVENTION

The invention defines a method for evaluating half carcasses, also known as sides, of slaughtered animals that are detected at the product entrance, classification points, or product exit in slaughterhouses and meat packing facilities, by optical image processing. As a rule, inside the slaughterhouses and meat packing facilities, these half carcasses are transported, hanging from a hook, by means of special transport systems. The evaluation presented here is designed in particular for sides of pork, but it is also suitable in principle for sides of cattle, sheep, goats, or other large and small slaughtered animals.

BACKGROUND OF THE INVENTION

In general, the sides of pork are registered, weighed and evaluated. The sides of pork are evaluated commercially by an appropriate official market classification. The thickness of the fat and of the flesh is detected at legally prescribed points specific to particular countries or states. For sorting purposes, a market value determination of the carcasses is made, as a rule; the finding is more conclusive if many further specific parameters are included, but usually these are not standardized.

German Patents DE 41 09 345 C2 and DE 44 08 604 C2 disclose an analysis or evaluation of carcass halves by means of image processing. In this processing, a photogrammetrical assessment of partial images of the carcass halves is done, beginning at the rumpbone. A disadvantage of such methods is that the rumpbone, as a prominent point in the picture of the carcass halves, is not adequately reliably selectable under the usual conditions in slaughterhouses, since because of mistakes in splitting the carcass that sometimes occur (if the division is not precisely in the plane of symmetry of the carcass), portions of the spinal column are missing from one half of the carcass or are covered with leaf fat, also known as pork flare, yet the spine is known to be located in only a narrow region of the plane of symmetry of the body of the animal. Another disadvantage is that selecting the spinal column is complicated and requires much computation by way of object analysis with predefined contour and object parameters.

SUMMARY OF THE INVENTION

The object of the invention is to develop a method that assures evaluation of carcass halves by image processing while overcoming the above disadvantages; in particular with a method that is simple to achieve in terms of computation, adequately reliable evaluation is intended to be accomplished, even if splitting errors mean that the plane of symmetry is missed when the carcasses are split.

This object is attained with the characteristics recited in claim 1. Further features of the invention will become apparent from the dependent claims.

The object is attained essentially in that for the photogrammetrical evaluation and assessment, only those body components that extend anatomically over a wide region relative to the plane of symmetry of the carcass and are reliably detectable visually are used; the hipbone, the gluteus medius muscle (MGM), in particular, and the back fat meet these requirements.

Because there are two hipbones, which meet solely in the plane of symmetry (inside the hip joint), the cut always runs through a hipbone and is thus optically visible and can be reliably evaluated by computation. Because it cannot be overlapped by leaf fat, the split surface cannot be visually concealed. The MGM and the back fat extend in the same over broad portions of the width of the back and are always reliably selectable visually and by computation by way of the transitions in brightness or color.

One advantageous exemplary embodiment of the invention is explained in further detail in conjunction with FIG. 1 in the form of photogrammetrical evaluation.

Reference numerals used

Figure 1:
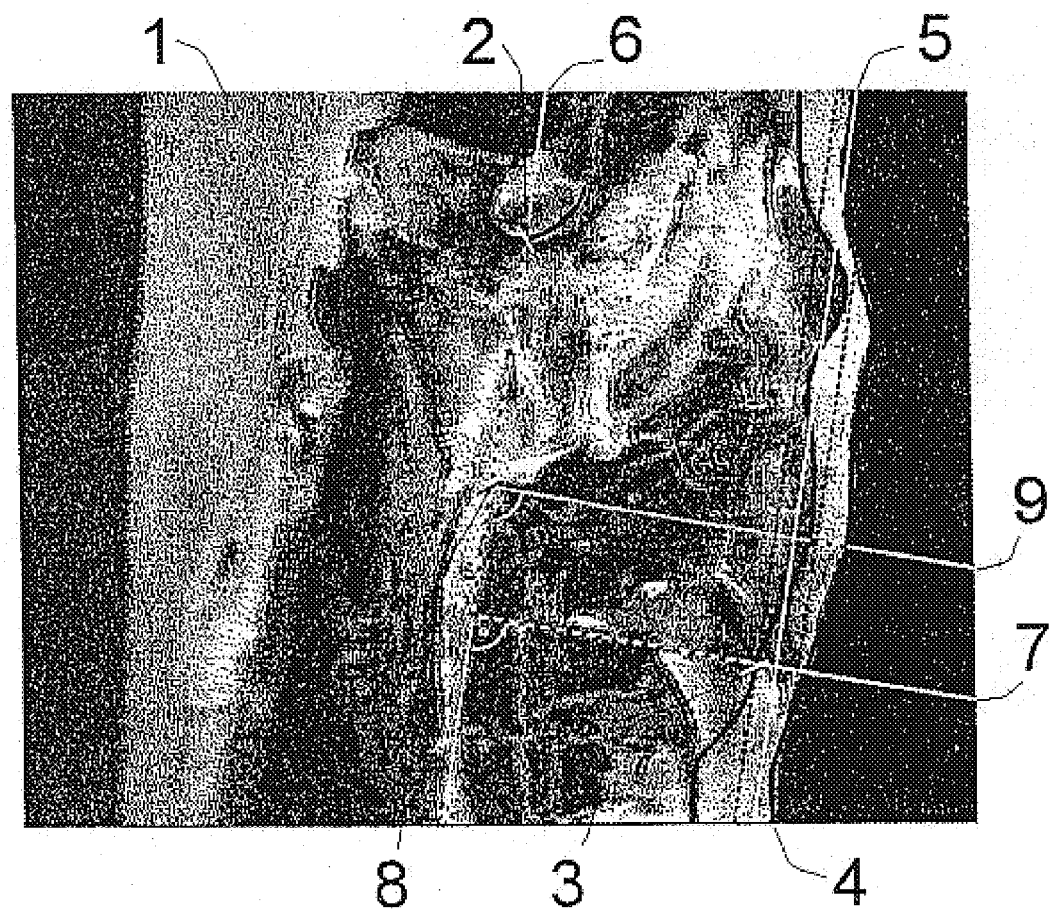
In FIG. 1, an image region 1 furnished for photogrammetrical evaluation includes an optical picture of the loin and leg region of the carcass half, including the end of the hipbone 2 nearer the body, the end of the MGM 3 nearer the body, and the outer boundary of the back fat 4. The oval-rounded hipbone (bright in front of a red peripheral region), which is readily visible and selectable by computation because of the transitions in brightness or color, is detected, and advantageously the end of the hipbone 2 nearer the body is made available, as a first prominent point, to the photogrammetrical evaluation. The back fat is also detected with respect to its boundaries on the basis of the brightness or color transitions (bright in front of a red peripheral region or background) and made available to the photogrammetrical evaluation in the form of a first straight line 5, in terms of its mean course. It is conceivable at the same time to detect its boundaries and the surface area or the width to be determined or detected, and to make a point of minimal fat thickness available as a second prominent point to the photogrammetrical evaluation. However, it is advantageous to detect the MGM 3 on the basis of the brightness or color transitions (red in front of a bright peripheral region) and to furnish the end of the MGM 3 nearer the body to the photogrammetrical evaluation as a second prominent point. Given a known side of the carcass half, the straight line 5 can be represented by computation as a parallel 6 through the first prominent point—in the form of the end of the hipbone 2 nearer the body—whereupon a vertical 7 through the second point is unequivocally determined; this vertical is advantageously calculated with respect to its segments as far as the parallel 6 and the outer boundary of the back fat 4. An advantageous refinement provides the calculation of the length from the first prominent point—in the form of the end of the hipbone 2 nearer the body—to the base point of the vertical 7; further base points 8 derived from this length can also be calculated—such as a point which divides this line in a ratio of 2:1 and by which further verticals 9 are determined—and their segments are advantageously calculated analogously. The calculated lengths of the segments or area values between them serve as specific parameters for evaluating the carcass half. It is especially advantageous, by way of this computationally reliable selection of two points and one direction, to simulate the classical two-point method in modified form photogrammetrically.

1 Image region
2 End of a hipbone nearer the body
3 End of the MGM nearer the body
4 Back fat
5 Straight line
6 Parallel
7 Vertical
8 Further base points
9 Further vertical

What is claimed is:

1. A method for evaluating carcass halves by optical image processing, in which an image region (1) furnished for photogrammetrical evaluation contains an optical picture taken of the loin and leg region of the carcass half, and readily visible body components are detected by computation and specific parameters for the evaluation are ascertained, characterized in that two prominent points and one straight line (5) are reliably detected photogrammetrically, with the end of an hipbone (2) nearer the body is used as a first prominent point, and the mean course of the back fat (4) is used as the straight line (5);

that a parallel (6) through the first prominent point and a vertical (7) through the second prominent point relative to the straight line (5) are calculated; and that the length of the segments of the vertical (7) to the parallel (6) and to the outer boundary of the back fat (4) are used as specific parameters for the evaluation.

2. The method for evaluating carcass halves by optical image processing of claim 1, characterized in that as the second prominent point, the point of minimal fat thickness of the back fat (4) or the end of the MGM (3) nearer the body is reliably detected photogrammetrically.

3. The method for evaluating carcass halves by optical image processing of claim 1 characterized in that the length of the distance on the parallel (6) from the first prominent point to the base point of the vertical (7) is calculated.

4. The method for evaluating carcass halves by optical image processing of claim 3, characterized in that from the calculated length of the distance, further base points (7) on the parallel (6) and further verticals (8) are calculated.

5. The method for evaluating carcass halves by optical image processing of claim 1, characterized in that a two-point method modified for reliable photogrammetrical detection is realized.

* * * * *